(12) United States Patent
Carmi et al.

(10) Patent No.: US 9,299,142 B2
(45) Date of Patent: Mar. 29, 2016

(54) PERFUSION IMAGING

(71) Applicant: KONINKLIJKE PHILIPS N.V., Eindhoven (NL)

(72) Inventors: Raz Carmi, Haifa (IL); Yechiel Lamash, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 14/350,374

(22) PCT Filed: Oct. 15, 2012

(86) PCT No.: PCT/IB2012/055594
§ 371 (c)(1),
(2) Date: Apr. 8, 2014

(87) PCT Pub. No.: WO2013/061202
PCT Pub. Date: May 2, 2013

(65) Prior Publication Data
US 2014/0254909 A1    Sep. 11, 2014

Related U.S. Application Data

(60) Provisional application No. 61/550,490, filed on Oct. 24, 2011.

(51) Int. Cl.
*G06K 9/00* (2006.01)
*G06T 7/00* (2006.01)
(Continued)

(52) U.S. Cl.
CPC .............. *G06T 7/0012* (2013.01); *A61B 5/026* (2013.01); *A61B 6/032* (2013.01); *A61B 6/486* (2013.01); *A61B 6/507* (2013.01); *A61B 6/5217* (2013.01)

(58) Field of Classification Search
None
See application file for complete search history.

(56) References Cited

U.S. PATENT DOCUMENTS

| 7,949,172 B2 | 5/2011 | Conti et al. | |
| 9,084,554 B2 * | 7/2015 | Jung et al. | 1/1 |

(Continued)

FOREIGN PATENT DOCUMENTS

WO    9114232 A1    9/1991

OTHER PUBLICATIONS

Imamura, T., et al.; Peak time difference of time-density curve in contrast media transit as an indicator of asymmetric cerebral perfusion; 1994; Journal of the Neurological Sciences; 126:197-201.
(Continued)

*Primary Examiner* — Shervin Nakhjavan (57) ABSTRACT

A perfusion imaging data processor (122) includes an agent peak characteristic-time determiner (206) configured to determine two or more agent peak characteristic-times respectively for two or more circulatory sub-systems represented in a same sub-set of voxels of a set of time-series data of perfusion imaging data, an agent peak argument determiner (210) configured to determine an agent peak argument for each of the two or more agent peak characteristic-times, an agent peak argument relation determiner (212) configured to determine a relationship between the agent peak arguments of the two or more agent peak characteristic-times, and a perfusion map generator (214) configured to generate, based on the determined relationship and the perfusion imaging data, at least one perfusion map, wherein the at least one perfusion map includes volumetric image data visually presenting at least one of a relationship or a difference between the two or more circulatory sub-systems.

25 Claims, 7 Drawing Sheets

(51) Int. Cl.
*A61B 6/03* (2006.01)
*A61B 6/00* (2006.01)
*A61B 5/026* (2006.01)

(56) References Cited

U.S. PATENT DOCUMENTS

| | | | |
|---|---|---|---|
| 2006/0025667 | A1 | 2/2006 | Ashton |
| 2008/0114234 | A1* | 5/2008 | Gering ............... 600/411 |
| 2008/0221441 | A1 | 9/2008 | Bjornerud et al. |
| 2008/0269595 | A1* | 10/2008 | Wong ............... 600/411 |
| 2009/0297008 | A1* | 12/2009 | Taxt et al. ............ 382/131 |
| 2010/0060644 | A1 | 3/2010 | Elie et al. |
| 2010/0128942 | A1 | 5/2010 | Licato et al. |
| 2010/0266190 | A1 | 10/2010 | Zagorchev et al. |
| 2010/0296714 | A1 | 11/2010 | Schmainda et al. |
| 2011/0105887 | A1 | 5/2011 | Gagnon et al. |
| 2012/0275674 | A1* | 11/2012 | Quelever et al. ........ 382/131 |
| 2012/0323118 | A1* | 12/2012 | Menon Gopalakrishna et al. ............ 600/431 |

OTHER PUBLICATIONS

Miles, K. A., et al.; Perfusion CT: a worthwhile enhancement?; 2003; The British Journal of Radiology; 76:220-231.

Miles, K. A., et al.; Functional images of hepatic perfusion obtained with dynamic CT; 1993; Radiology; 188(2).

Niu, X., et al.; Detectability of perfusion defect in five-dimensional gated-dynamic cardiac SPECT images; 2010; Med. Phys.; 37(9)5102-5112.

* cited by examiner

PERFUSION IMAGING

CROSS REFERENCE TO RELATED APPLICATIONS

This application is a national filing of PCT application Serial No. PCT/IB2012/055594, filed Oct. 15, 2012, published as WO 2013/061202 A2 on May 2, 2013, which claims the benefit of U.S. provisional application Ser. No. 61/550,490 filed Oct. 24, 2011, which is incorporated herein by reference.

The following generally relates to a perfusion imaging and is described with particular application to computed tomography (CT); however, the following is also amenable to other imaging modalities such as MRI, PET, SPECT, US, optical tomography, and/or other imaging modalities.

Perfusion imaging, and the related terms permeability imaging, dynamic contrast imaging or first-pass scans, are known techniques to image and evaluate parameters which are related to the blood flow within the patient body. Perfusion imaging can be used to detect both physical structures within the body and tissue function and viability. Perfusion imaging is useful for studying patients with brain or heart damage, e.g. as a result of stroke or infract; patients with cancer disease in organs such as the liver, lungs, pancreas and others; and general organ functionality in organs such as lungs, liver and kidneys. Perfusion imaging has the potential to be an important tool for quantitatively assessing many types of cancer and tumors. Since perfusion imaging basically measures blood flow characteristics, several imaging modalities can be used with the appropriate administered contrast materials. For example, perfusion imaging can be done by CT with iodine contrast agent, MRI with gadolinium or iron-oxide contrast agent, PET and SPECT with several types of radiotracers, and ultrasound with micro-bubbles contrast agents. In animal pre-clinical imaging, optical tomography with fluorescent agents is applicable as well.

Perfusion imaging techniques usually require repeated imaging of the volume of interest for a number of different time points, for example between 3-30 repeated scans with a few seconds difference between successive scans (e.g. 1 to 10 sec per time frame). In common perfusion techniques, a bolus of a contrast agent is administered into the patient's vascular system, for example by an automatic injector, and images from the region of interest are collected for a period covering the transit of the contrast agent bolus through the tissue in the region of interest. The changes of the contrast agent local concentration (as can be inferred from image data) along time are used for analyzing physiological parameters. In clinical practice, it is common for the perfusion image series to be inspected qualitatively or to be assessed quantitatively with special analysis algorithms. A quantified result may include, for a region or per voxel, an absolute measurement of blood flow, blood volume, mean transit time, time of arrival, permeability surface product, time to peak, peak intensity, maximal gradient and other parameters. Such blood flow and vascularization arguments can be represented by a structure referred herein to the general term 'perfusion map'.

The particular interest for using perfusion in cancer diagnostics is mainly related to the angiogenesis phenomenon. Angiogenesis occurs in the healthy body for healing wounds and for restoring blood flow to tissues after injury or insult. Typically, normal vascularity develops with the intent of providing nutrients to body tissues, and normal vessels evolve so that equilibrium is established between vessel growth and cellular demands. It is well known that cancerous tissue development is associated with excess angiogenesis in the surrounding of that tissue. The newly formed vessels can further lead to hyper-proliferation of the tumor cells. Thus, early detection and follow-ups during treatment, of abnormal angiogenesis is critical to reducing morbidity and mortality rates associated with various cancers. Perfusion studies may also allow measuring the permeability of blood vessels in tumor regions, which is considered as important factor since usually blood vessels in cancerous tissues tend to leak into the intracellular space much more than normal blood vessels.

With regards to cancer diagnostics, MRI and CT are very effective in determining anatomy features. However they usually convey little information about the functional status of the tumor tissue or adjacent tissue (e.g. degree of angiogenesis, tissue viability, malignancy, etc). Although tumor malignancy to some extent may be suggested indirectly by contrast enhanced imaging, several studies have shown that the degree of contrast enhancement is by no means a reliable indicator of tumor grade. PET and SPECT imaging usually show functional parameters of the imaged tissues. However, in many cases this information is insufficient. For example, the common FDG-PET examination used in oncology often cannot tell accurately the staging of cancer or its response to medical treatment.

Perfusion imaging of tumors is used to demonstrate the vascular growth (angiogenesis and neovascularization) associated with tumor growth by imaging for example the blood volume (BV) or blood flow (BF) in a tumor. Since BV values correlate with the grade of vascularity; high-grade (malignant) tumors tend to have higher BV values than low-grade (less malign) tumors. Neovascularization also influences the dissemination of cancer cells throughout the entire body eventually leading to metastasis formation. The vascularization level of a solid tumor is thought to be an excellent indicator of its metastatic potential. By measuring the vascularity levels, perfusion imaging is therefore helpful in characterizing the tumor. It can also help in selection of therapy procedure (e.g. anti-angiogenesis drug/radiotherapy/chemotherapy) and prediction of its success.

Tumor perfusion imaging is potentially useful in the diagnostics of several cancer types and in different organs. However, there are still significant obstacles for achieving a reliable clinical application, such as issues of consistency of the results, accurate quantification, analysis standardization, optimizing clinical protocol, patient motion, image artifacts and both radiation and contrast agent dose reduction. Furthermore, the imaging system technical capabilities of today are not always sufficient. Moreover, with conventional perfusion analysis approaches, a thorough analysis of regional blood flow characteristics is provided and visualized, but these approaches do not differentiate between different circulatory sub-systems in the same region and do not show the unique relations between those circulatory sub-systems. Unfortunately, even a single image voxel can include data that represents the flow pattern of more than one circulatory sub-system, sometimes interfering one with the other. In addition, the signal noise and/or other practical inaccuracies may be quite significant, further complicating the analysis.

Aspects described herein addresses the above-referenced problems and others.

In one aspect, a perfusion imaging data processor includes an agent peak characteristic-time determiner configured to determine two or more agent peak characteristic-times respectively for two or more circulatory sub-systems represented in a same sub-set of voxels of a set of time-series data of perfusion imaging data. The processor further includes an agent peak argument determiner configured to determine an agent peak argument for each of the two or more agent peak characteristic-times. The processor further includes an agent peak argument relation determiner configured to determine a relationship between the agent peak arguments of the two or more agent peak characteristic-times. The processor further includes a perfusion map generator configured to generate, based on the determined relationship and the perfusion imaging data, at least one perfusion map, wherein the at least one perfusion map includes volumetric image data visually presenting at least one of a relationship or a difference between the two or more circulatory sub-systems.

In another aspect, a method includes determining, with a processor, at least one of a relationship or a difference between agent peak arguments corresponding to two or more agent peak characteristic-times, which correspond to two or more different circulatory sub-systems represented in a same sub-set of voxels of a set of time-series data of perfusion imaging data, based on the same sub-set of voxels, and visually presenting at least one of the relationship or the difference.

In another aspect, a method includes generating a perfusion map including imaging data which visually illustrates at least one of a relationship or a difference between two or more agent peaks in a same group of voxels of perfusion imaging data.

The invention may take form in various components and arrangements of components, and in various steps and arrangements of steps. The drawings are only for purposes of illustrating the preferred embodiments and are not to be construed as limiting the invention.

The following generally relates to determining relations and/or differences between two or more circulatory sub-systems represented in perfusion imaging data and generating information indicative thereof. Examples of circulatory sub-systems include, but are not limited to, the pulmonary circulation sub-system, the systemic circulation sub-system, the hepatic portal circulation sub-system, and the coronary circulation sub-system. With organs such as the heart, the lungs and the liver, two circulatory sub-systems may be active in the same organ. Generally, in organs, arteries divide to smaller arteries which in turn divide to form capillaries, which unite to form larger vessels which in turns leave the tissues and join to form veins, which leave the organs and eventually join the vena cava.

In the pulmonary circulation sub-system, the pulmonary artery arises from the heart right ventricle and transports deoxygenated blood to the lungs, where the blood becomes oxygenated. The pulmonary veins return the oxygenated blood to the left atrium of the heart. In the systemic circulation sub-system, oxygenated blood is pumped from the heart's left ventricle into the aorta. Branches of the aorta convey blood to most of the tissues and organs of the body. The tissue cells are oxygenated, and then deoxygenated blood returned to the heart via the vena cava. In addition, the toxic carbon-dioxide is conveyed out from the cells. The blood then flows into the right ventricle, from where it joins the pulmonary circulation.

The hepatic portal circulation sub-system serves the intestines, spleen, pancreas and gall bladder. The liver receives its blood from two main sources: the hepatic artery (a branch of the aorta) which supplies oxygenated blood to the liver, and the hepatic portal vein which is formed by the union of veins from the spleen, the stomach, pancreas, duodenum and the colon. The hepatic artery and hepatic portal vein open into the liver sinuses where the blood is in direct contact with the liver cells. The deoxygenated blood eventually flows into the vena cava via the hepatic veins. The coronary circulation sub-system supplies the heart muscle with oxygen and nutrients and conveys carbon dioxide and other waste products away from the heart.

Suitable perfusion imaging data includes CT, MRI, PET, SPECT, US, optical tomography and/or other perfusion imaging data. For explanatory purposes and sake of brevity, the following describes the system and/or method in relation to CT perfusion imaging data. Initially referring to FIG. 1, an imaging system 100 such as a computed tomography (CT) scanner is illustrated. The imaging system 100 includes a stationary gantry 102 and a rotating gantry 104, which is rotatably supported by the stationary gantry 102. The rotating gantry 104 rotates around an examination region 106, and a portion of an object or subject therein, about a longitudinal or z-axis.

Figure 1:
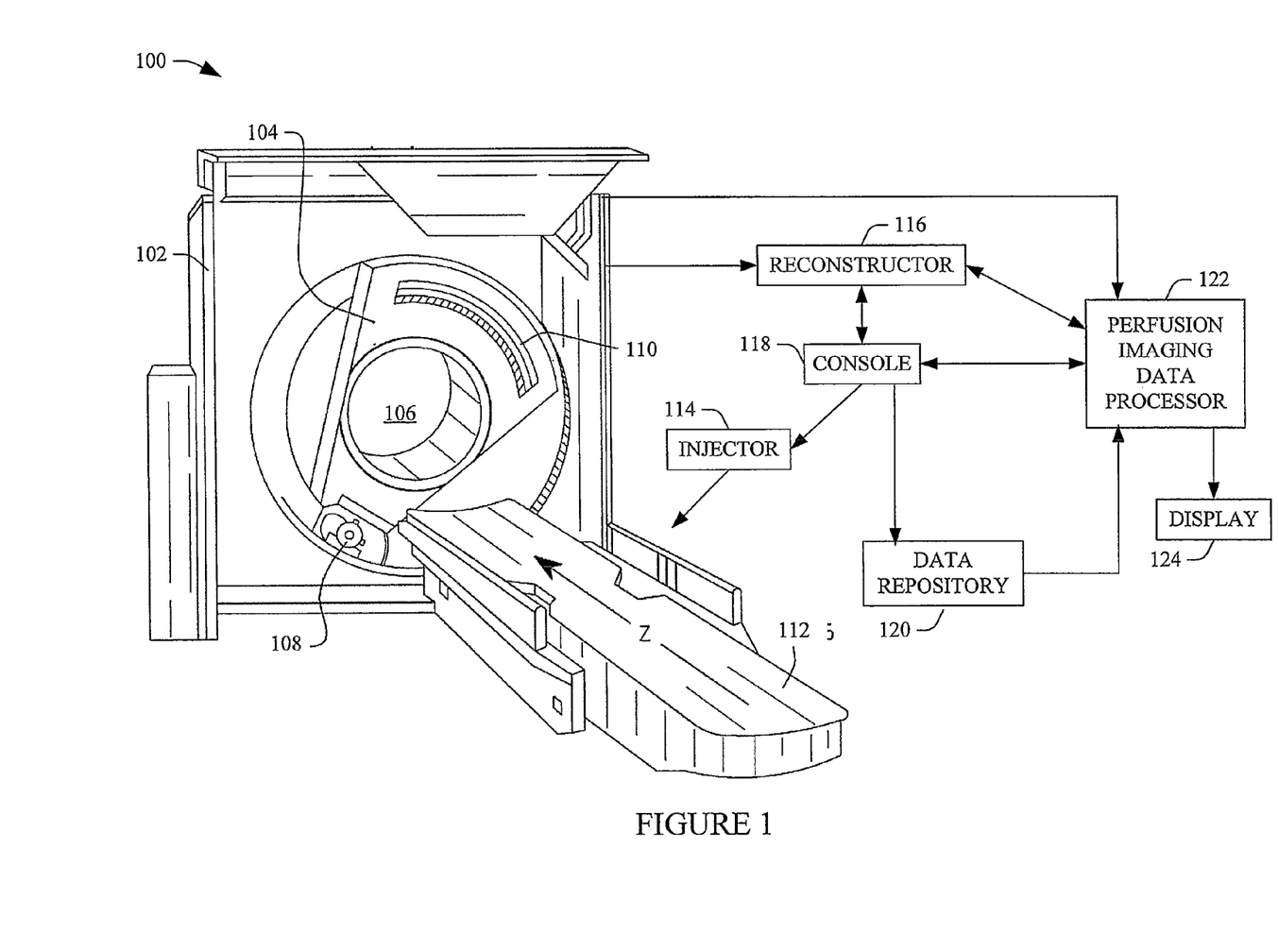
FIG. 1 schematically illustrates an example imaging system in connection with a perfusion imaging data processor.

A radiation source 108, such as an x-ray tube, is supported by and rotates with the rotating gantry 104 around the examination region 106. The radiation source 108 emits radiation that is collimated to form a generally fan, wedge, or cone shaped radiation beam that traverses the examination region 106. A radiation sensitive detector array 110 detects photons emitted by the radiation source 108 that traverse the examination region 106 and generates projection data indicative of the detected radiation. The radiation sensitive detector array 110 includes one or a two dimensional array of detector pixels.

A subject support 112, such as a couch, supports the subject 108 or an object in the examination region 106 and is movable along the x, y and z-axis directions in coordination with the rotation of the rotating gantry 104 to facilitate helical, axial, or other desired scanning trajectories. An injector 114 is configured to inject or administer a material such as one or more contrast agents to a subject or an object to be scanned. A contrast agent can additionally or alternatively be manually administered by a clinician or the like. Where the contrast agent is manually administered, the injector 114 can be omitted.

A reconstructor 116 reconstructs the projection data and generates time series volumetric image data indicative of the examination region 106. Various reconstruction algorithms can be employed such as filtered backprojection, statistical, iterative, sparse sampling, and/or other reconstruction algorithms. A general purpose computing system serves as an operator console 118. Software resident on the console 118 and executed by a processor allows an operator to control operation of the system 100, for example, by allowing the operator to select an imaging protocol such as a perfusion protocol, initiate scanning, etc, A data repository 120 can be used to store the imaging data generated by the system 100. The data repository 120 may include one or more of a picture archiving and communication system (PACS), a radiology information system (RIS), a hospital information system (HIS), an electronic medical record (EMR) database, a server, a computer, and/or other data repository. The data repository 120 can be local to the system 100 (as shown) or remote from the system 100.

A perfusion imaging data processor 122 is configured to process perfusion imaging data such as perfusion imaging data from the system 100 and/or the data repository 120. As described in greater detail below, the perfusion imaging data processor 122 determines relations and/or differences between two or more circulatory sub-systems represented in the perfusion imaging data and generates information indicative thereof. In one instance, the generated information provides better results and/or improves results relative to a configuration in which the perfusion imaging data processor 122 is not used or is omitted. The results may facilitate detection of tumors, characterization of tumors (e.g., vascularity level, aggression, potential for metastasis, etc.), therapy selection, predication of therapy success for several therapy types, follow up studies (especially when using anti-angiogenesis drug for therapy), etc.

A display 124 is configured to visually present information generated by at least the perfusion imaging data processor 122.

It is to be appreciated that the perfusion imaging data processor 122 can be implemented via a processor executing one or more computer readable instructions encoded or embedded on computer readable storage medium such as physical memory. Such a processor can be part of the console 118 and/or other computing device. Additionally or alternatively, the processor can execute at least one computer readable instructions carried by a carrier wave, a signal, or other non-computer readable storage medium such as a transitory medium.

Figure 2:
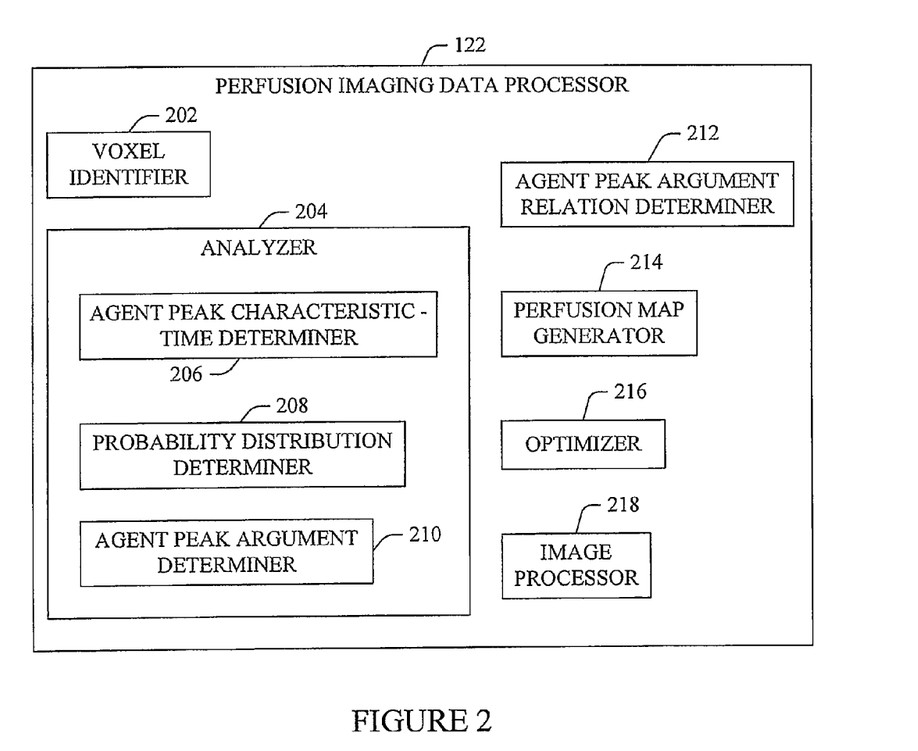
FIG. 2 schematically illustrates an example of the perfusion imaging data processor 122.

FIG. 2 schematically illustrates an example of the perfusion imaging data processor 122. In the illustrated embodiment, the perfusion imaging data processor 122 obtains perfusion imaging data from the system 100, the data repository 120 and/or other device.

A voxel identifier 202 is configured to identify one or more groups of one or more voxels in the obtained imaging data to process. The voxel identifier 202 can employ automated approaches and/or utilize user input to identify the one or more groups of the one or more voxels.

An analyzer 204 includes one or more of an agent peak characteristic-time determiner 206, a probability distribution determiner 208, or an agent peak argument determiner 210.

The agent peak characteristic-time determiner 206 is configured to determine an agent peak characteristic-time corresponding to a time of peak agent uptake in a generally tubular structure (e.g., a vessel or a mesh of vessels) in a subject or object as a function of time from the group of voxels. Such a peak may be identified based on intensity, gradient and/or otherwise. For multiple agents and/or peaks, a characteristic-time is determined for one or more of the agents and/or peaks.

The probability distribution determiner 208 is configured to determine a probability distribution for each of the agent peak characteristic-times in which the probability distribution indicates a probability of a peak being the "true" peak. For instance, due to inaccuracies, noise, etc. the location of a peak may not be definitive, so several or a range of candidate characteristic-times are determined for each peak, each with a different probability.

In this embodiment, the agent peak characteristic-time determiner 206 and/or the probability distribution determiner 208 utilizes an initial model to determine multiple peaks. This model may include peak shapes, magnitudes, constraints, etc. Generally, the model is applicable for a vector of image values (or signal) versus time and/or other representation.

The agent peak characteristic-time determiner 206 and/or the probability distribution determiner 208 can determine peak characteristic-times also using information such as a time at which a contrast material of interest first appears in the imaging data, an estimation of cardiac/aorta input function, prior information on administered agent concentration and volume, etc.

The agent peak argument determiner 210 is configured to determine, for a peak characteristic-time, one or more peak arguments such as peak intensity, peak gradient, a value indicative of an integral in the vicinity of the peak, the time to peak relative to the peak time of the aorta or vena cava, etc. The peak arguments can be also normalized, for example, with the aorta peak and/or other information.

A peak argument relation determiner 212 is configured to determine relations between the arguments of two or more different peaks. This includes, but is not limited to, selecting a predominant peak between first and second peaks along time, Hepatic Portal Index (HPI), weighted arterial perfusion, etc.

A perfusion map generator 214 generates a perfusion function map, which can be represented as a volumetric imaging data where each voxel or region represents a value of a relation. The volumetric data can be organized, for example, as a set of two-dimensional images (superimposed or separate) where each image corresponds to a slice along the z-axis and/or otherwise.

An optimizer 216 is configured to optimize the perfusion map using an iterative or non-iterative optimization approach.

An image processor 218 processes at least the perfusion map and visually presents the function map via the display 124 and/or other device. For example, in one instance color hue can be used to represent one peak argument (or relation of multiple arguments) and the color intensity can be used to represent another argument or multiple argument relations. Optionally, the colored image can be fused in a semi-transparent manner with a grayscale image (which can represent anatomical information or other information).

Alternatively, a single argument or argument relation function is visualized by a color scale (e.g., in full intensity) or by a grayscale. In another instance, two or more arguments or argument relation functions are visualized in separated images (e.g. one near the other). Additionally or alternatively, other information can be shown in a graph (e.g. time-activity curves), a histogram (e.g. statistics of voxels in a larger ROI), and/or other visual form.

Figure 3:
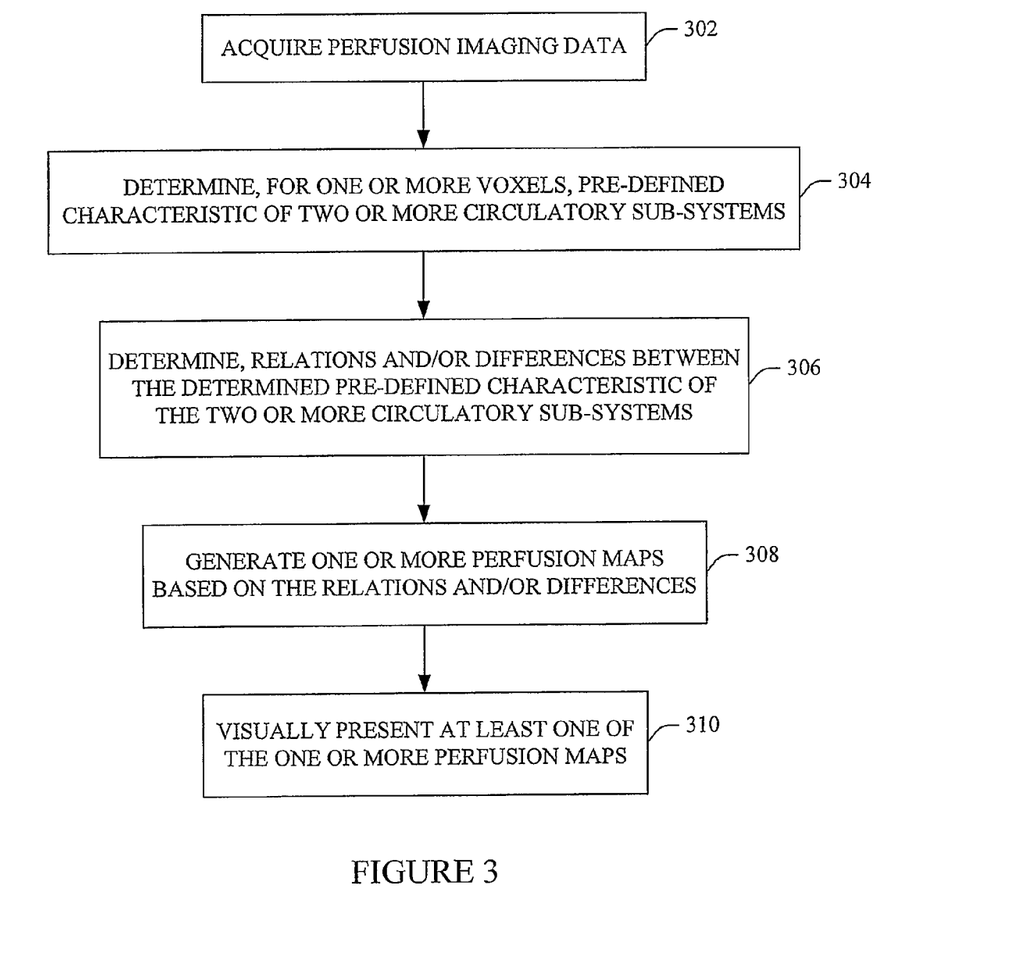
FIG. 3 illustrates an example method for evaluating perfusion imaging data.

FIG. 3 illustrates an example method for evaluating perfusion imaging data. It is to be appreciated that the ordering of the acts in the methods described herein is not limiting. As such, other orderings are contemplated herein. In addition, one or more acts may be omitted and/or one or more additional acts may be included.

At 302, imaging data from a perfusion scan is obtained. Generally, the imaging data includes reconstructed time series volumetric data, including spatial registration between data acquired at different times. The imaging data may or may have been processed via one or more corrections and/or other post-processing. As described herein, the perfusion imaging data can include CT, MRI, PET, SPECT, US and/or other perfusion imaging data, and can be obtained from an imaging system and/or data repository.

At 304, the perfusion imaging data processor 122 evaluates the imaging data and determines, for a set of one or more voxels or regions of voxels of interest, pre-defined characteristics of two or more different circulatory sub-systems represented and active in the same region of organ or tissue.

At 306, the perfusion imaging data processor 122 determines pre-defined relations and/or differences between determined characteristics of the two circulatory sub-systems. In one instance, an iterative optimization is utilized to improve a robustness of the relations and/or differences against noise and other inaccuracies and limitations. For example, the iterative optimization may simultaneously improve objective map conditions (e.g. by total-variation minimization approach) and maximize probabilities that perfusion characteristics of the circulatory sub-systems will fit a pre-defined model and constraints.

At 308, one or more (e.g., voxel-wise) perfusion maps are generated based on the relations and/or differences.

At 310, at least one of the one or more perfusion maps is visually presented.

Figure 4:
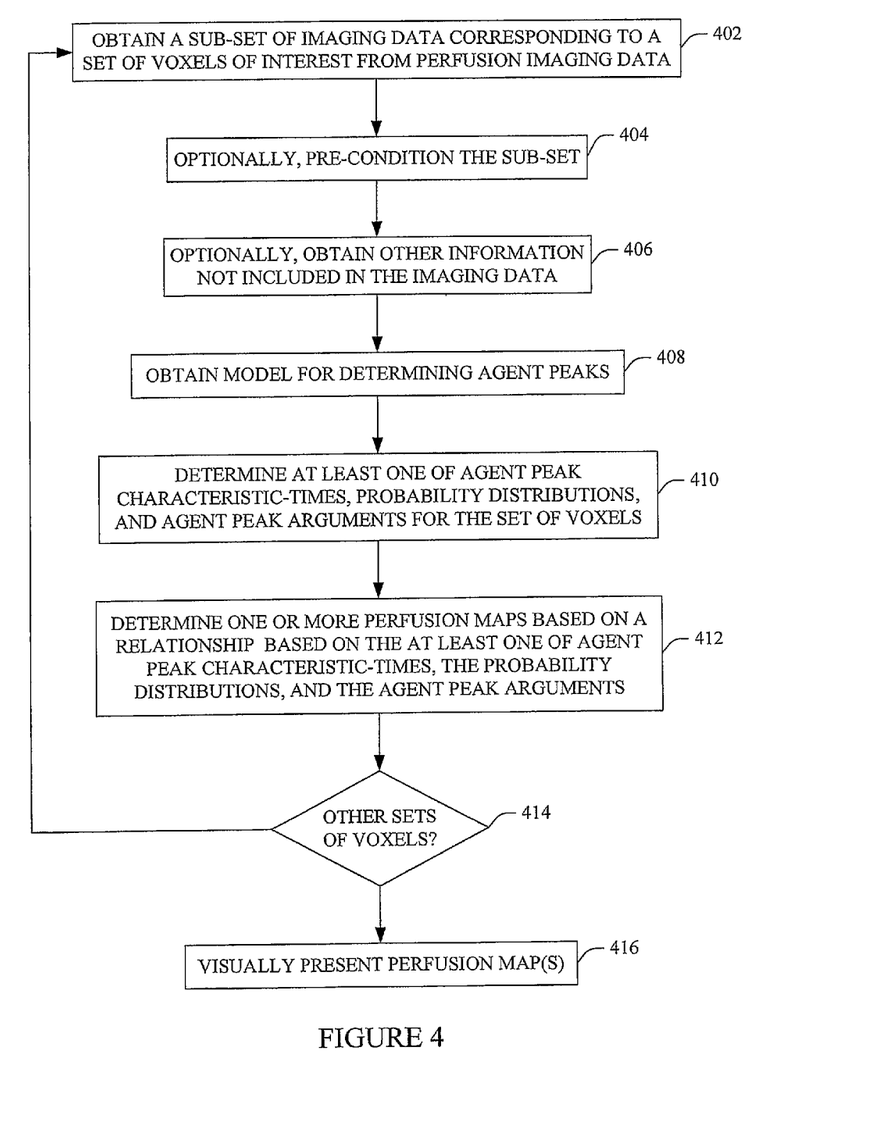
FIG. 4 illustrates another example method for evaluating perfusion imaging data.

FIG. 4 illustrates another example method for evaluating perfusion imaging data. Likewise, it is to be appreciated that the ordering of the acts in the methods described herein is not limiting. As such, other orderings are contemplated herein. In addition, one or more acts may be omitted and/or one or more additional acts may be included.

At 402, a sub-set of imaging data corresponding to a set of voxels (e.g., one or a group of more than one) is obtained from perfusion imaging data. This may include obtaining imaging data for one or more voxels through a sub-set of or the entire time-series of the perfusion imaging data. This can be through manual and/or automated approaches.

At 404, optionally, the sub-set of imaging data is pre-conditioned. This may include filtering, de-noising, spatial smoothing, temporal smoothing, re-sampling, spatial co-registration along of the time series, motion correction, de-convolving, normalizing and/or other processing.

At 406, optionally, other information not included in the imaging data, such as information about a contrast agent, a patient, one or more previous studies, etc., is obtained. Such information may include a time at which the administered contrast material first appears in the imaging data, a concentration of the administered contrast material, a weight of the subject or object, an estimation of a cardiac/aorta input function, etc.

At 408, a model for determining agent peaks is obtained. The model can include peak shapes, magnitudes, constraints, an algorithm for determining contrast material peak characteristic-time, an algorithm for determining a probability distribution for contrast material peak characteristic-time, an algorithm for determining contrast material peak arguments, etc.

At 410, at least one of agent peak characteristic-times, probability distributions of the agent peak characteristic-times and/or agent peak arguments for the agent peak characteristic-times are determined for the sub-set of voxels.

At 412, one or more perfusion maps are generated based on the agent peak characteristic-times, the probability distributions of the agent peak characteristic-times and/or the agent peak arguments for the agent peak characteristic-times.

At 414, if there is another set of voxels to evaluate, acts 402 to 412 are repeated. Alternatively, acts 402 to 412 can be concurrently performed in parallel for multiple identified sets of voxels of interest.

At 416, at least one of the one or more perfusion maps is visually presented, as described herein.

Figure 5:
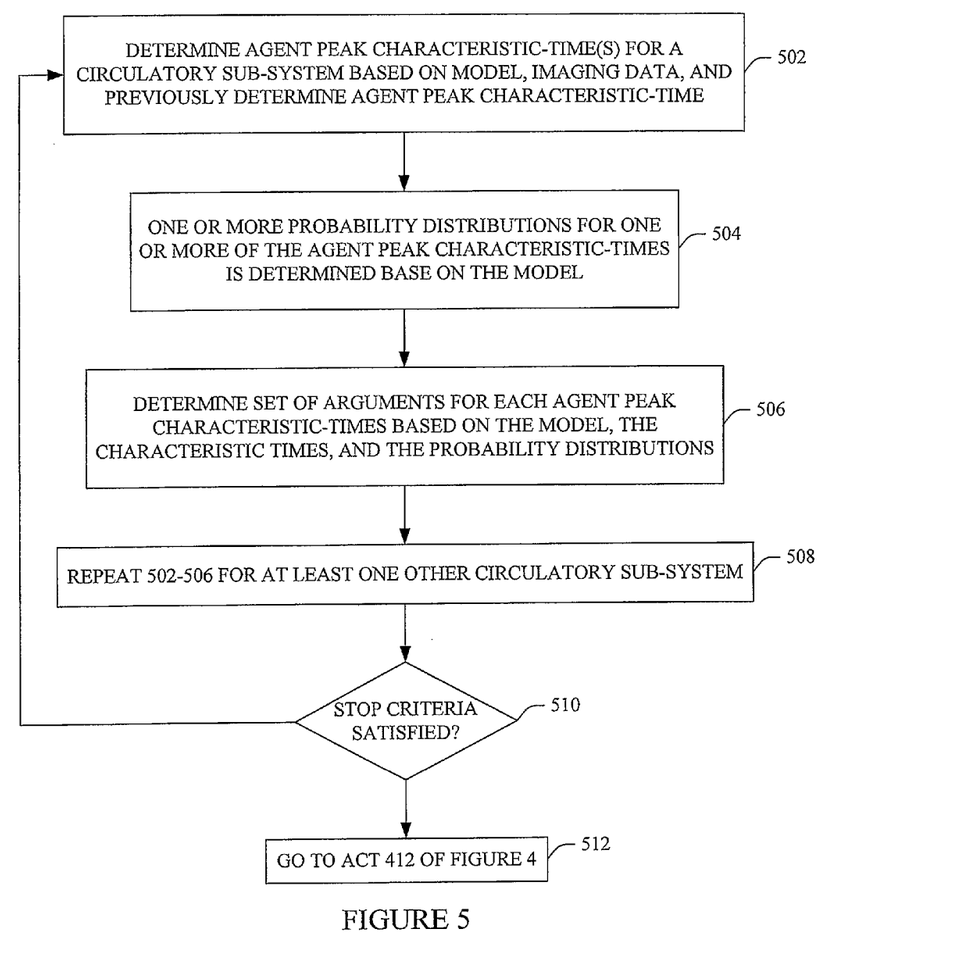
FIG. 5 illustrates an example iterative method for determining agent peak characteristic-times and peak arguments.

FIG. 5 illustrates an example of act 410 of FIG. 4. It is to be appreciated that the ordering of the acts in the methods described herein is not limiting. As such, other orderings are contemplated herein. In addition, one or more acts may be omitted and/or one or more additional acts may be included.

At 502, one or more agent peak characteristic-times of blood flow peak corresponding to a circulatory sub-system are determined based on the model, the sub-set of imaging data and any peak characteristic-times already determined.

At 504, one or more probability distributions for the one or more determined agent peak characteristic times are generated based on the model.

At 506, a set of arguments for each of the determined agent peak characteristic-times is determined based on the model, the one or more agent peak characteristic-times, and the probability distributions. This may include fitting the imaging data to a gamma-variate model based on a genetic algorithm where the characteristic-time is a fixed constraint.

At 508, acts 502 to 506 are repeated at least once for at least one other circulatory sub-system. Compliance with a set of mutual peak constraints and/or consistency criteria can be checked.

At 510, if stopping criteria is not satisfied, acts 502 to 508 are repeated. The stopping criteria may be based on a difference between sequential results and a predetermined stop threshold, a number of iterations, a lapse of time and/or other stopping criteria.

Otherwise, at 512, the agent characteristic-times, the probability distributions, and/or the set of arguments are utilized in connection with act 412 of FIG. 4.

In a variation, act 506 is performed after act 510.

Figure 6:
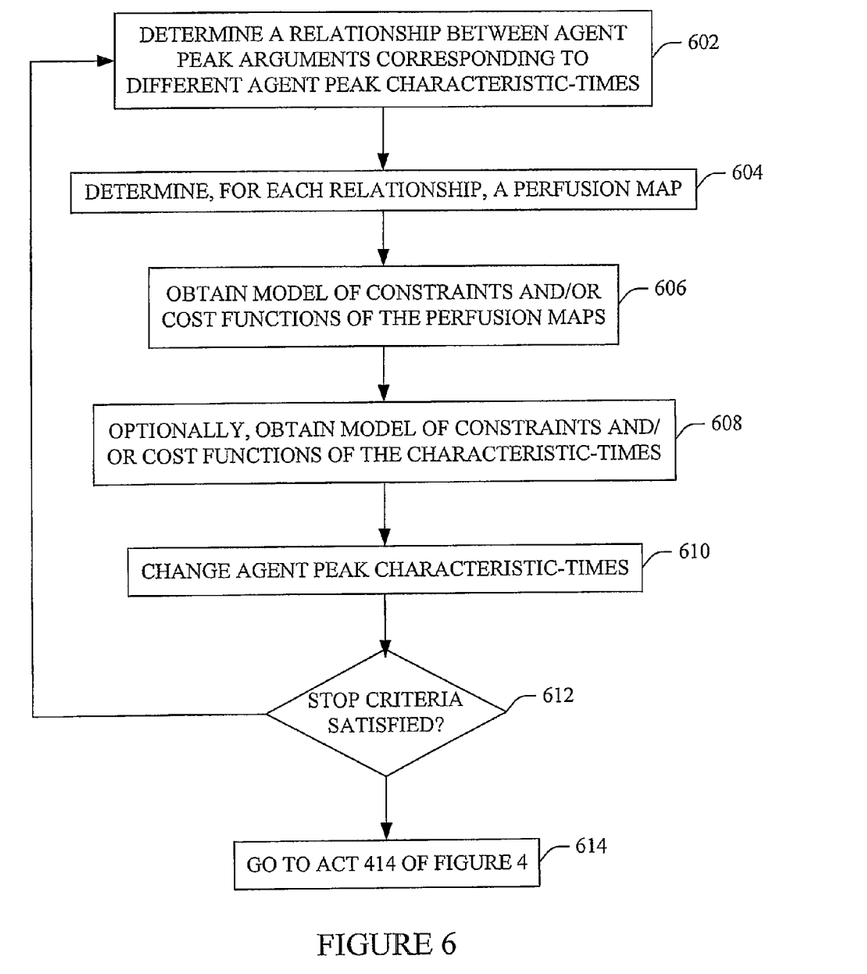
FIG. 6 illustrates an example iterative method for determining perfusion maps.

FIG. 6 illustrates an example of act 412 of FIG. 4. It is to be appreciated that the ordering of the acts in the methods described herein is not limiting. As such, other orderings are contemplated herein. In addition, one or more acts may be omitted and/or one or more additional acts may be included.

At 602, at least one relationship between agent peak arguments for each of different agent peak characteristic-times is determined corresponding to temporarily selected different agent peak characteristic times.

At 604, for each relationship, a perfusion map is generated.

At 606, a model of constraints and cost functions on the perfusion map is obtained. For example, a cost function on the map can include a summation on the map spatial gradients and/or any version of a total variation technique.

At 608, optionally, mutual constraints and/or cost functions on the characteristic-times are obtained. For example, a constraint on the characteristic-times can include a definition that during an attempt to optimize the selection of the characteristic-times, the time difference between two such times should be within a certain time range.

At 610, the agent peak characteristic-times are changed to simultaneously improve multiple relation function map image conditions subjected to the pre-determined constraints or cost functions and to increase the total probability of the selected characteristic-times, based on the models of act 606 and/or 608. This can be achieved via one or more of a gradient-descent, a genetic algorithm or other optimization techniques, including those which can compromise between global minimization of two or more dependent functions.

At 612, if stopping criteria is not satisfied, then acts 602 to 610 are repeated. The stopping criteria may be based on a difference between sequential results and a predetermined stop threshold, a number of iterations, a lapse of time and/or other stopping criteria.

Otherwise, if the stopping criteria are satisfied, then at 614 act 414 of FIG. 4 is performed.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The following provides a non-limiting example in the context of multiple circulatory sub-systems. For explanatory purposes, clarity, and sake of brevity, the following is described in connection with two agent peak characteristic times and two argument relationships. However, it is to be understood that the following can be extended to more or less agent peak characteristic-times, more or less argument relationships, and/or one or more other variables.

For each time-attenuation-curve (TAC) of each voxel: 1) determine the first initial characteristic-time $t^0_A$ and the second initial characteristic time $t^0_B$, according to the input data and the defined model; 2) determine the probability distributions $P(t^0_A)$, $P(t^0_B)$; 3) determine perfusion arguments and their relation functions: $F_1(t_A, t_B)$, $F_2(t_A, t_B)$, and 4) from all combinations of $t_A$, $t_B$, their probabilities and their mutual constraints (defined by a model), calculate the probabilities for each perfusion relation function $P(F_1)$, $P(F_2)$ and for each relation function mutual combination $P(F_1, F_2)$. The probability distributions may have in-principle non-regular shape (e.g. not bell-shape, non-symmetric, non-continuous, etc.).

A global minimization argument is then determined based on a total-variation approach. An example of such an argument is shown in ARGUMENT 1:

$$\underset{F_1,F_2}{\operatorname{argmin}}\left\{ k_1 \sum_i^V |\nabla F_{1i}| + k_1 \sum_i^V \lambda_{1i}(F_{1i}, F_{2i}) \cdot |F_{1i} - F^0_{1i}|^r + \right.$$
$$\left. k_2 \sum_i^V |\nabla F_{2i}| + k_2 \sum_i^V \lambda_{2i}(F_{1i}, F_{2i}) \cdot |F_{2i} - F^0_{2i}|^r \right\} \quad \text{ARGUMENT 1}$$

where $k_1$ and $k_2$ are weighting factors, i is an index run over all voxels in a volume V, $\nabla F$ represents a gradient of F, r is an exponent where r is a real number (e.g., r=1, 2, 3.25, etc.), and $\lambda_1$ and $\lambda_2$ are fidelity weights for each voxel in the respective relation function map.

In ARGUMENT 1, there are two terms for each relation function map (i.e. for each perfusion map), one is a total variation term (with a gradient of F) and the other is a fidelity term. Each term includes summation on all map voxels and may be applied in 2D or 3D. An iterative optimization process should find the final maps of $F_1$ and $F_2$ such that the whole expression is minimized. The fidelity weights $\lambda_1$ and $\lambda_2$ may be varied in each iteration step of the minimization process according to EQUATION 1:

$$\lambda^{m+1}_{1i} = h_1\left[(1-q_1)\frac{P(F^0_{1i})}{P(F^m_{1i})} + q_1\frac{P(F^0_{1i}, F^0_{2i})}{P(F^m_{1i}, F^m_{2i})}\right] \quad \text{EQUATION 1}$$
$$\lambda^{m+1}_{2i} = h_2\left[(1-q_2)\frac{P(F^0_{2i})}{P(F^m_{2i})} + q_2\frac{P(F^0_{1i}, F^0_{2i})}{P(F^m_{1i}, F^m_{2i})}\right]$$

where $h_1$ and $h_2$ are functions which are linear in a determined range and may also have a constant bias or a saturation range, m is the iteration index, and $q_1$ and $q_2$ are coupling factors (ratios) between $F_1$ and $F_2$. Where $\lambda$ is larger, there is a "pressure" to shift the intermediate F value toward its initial value, and where $\lambda$ is smaller, there is more freedom to change its value in order to minimize the local map gradients.

Figure 7:
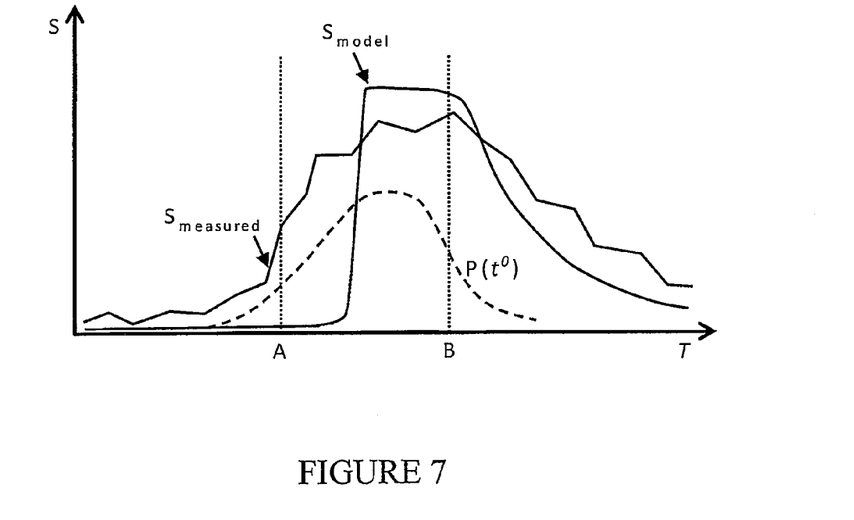
FIG. 7 graphically illustrates an example of the evaluation.

The above is further discussed in connection with the example in FIG. 7. In FIG. 7, a voxel TAC $S_{measured}$ shows a response that is assumed to represent a single peak flow. The example data includes noise and does not show a sharp peak. According to a specific model, the time to peak (TTP) and the maximal peak value (Emax) are to be determined. However, the model may define that the TTP is best determined by the time to the maximal gradient and the maximal enhancement value as the global maximal value in the selected time range. The two definitions may be coinciding in the ideal case of the theoretical TAC $S_{model}$.

In the measured TAC, the initial TTP is determined by the time A, and the maximal enhancement is determined by the time B. The characteristic time of the assumed single peak may be defined by the probability $P(t^0)$. It is possible to calculate independent probability distributions for each function $P(TTP)$ and $P(Emax)$, for example, directly from) $P(t^0)$. It is also possible to determine mutual probability distribution $P(TTP, Emax)$. For example, where the data deviates from the model, not because of noise or artifacts but due to a real complicated behavior of the sample, only the measured combinations of t and S are utilized (each will have a certain probability, but other theoretical combinations will have zero probability).

Generally, parts of the deviations from the model are due to noise or artifacts, and others are due to true different physical behavior. For the optimization process, the required level of coupling between the two functions (by the parameters $q_1$, $q_2$) can be predetermined. In principle, if the noise and artifacts are relatively large, the coupling ratio can be reduced (e.g., smaller q). However, if noise is minimal but the true behavior is more complicated than the simple model, the coupling between the TTP to Emax can be increased (e.g., increase q).

Figure 8:
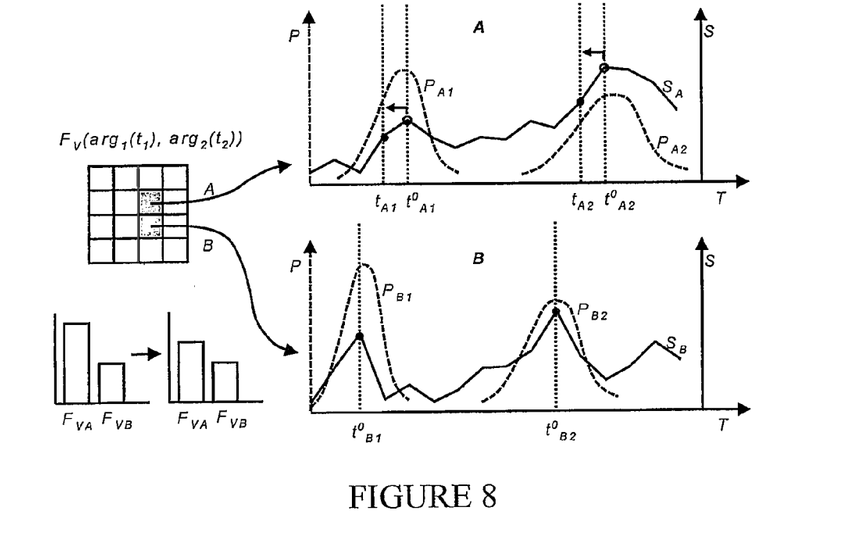
FIG. 8 graphically illustrates an example of the optimization.

FIG. 8 graphically illustrates an example of the optimization process. In this illustration, $F_v$ represents one peak argument relation function map calculated for a volume of interest. $F_v$ is a function of the arguments related to the two peaks. For the simplicity of the explanation, two neighbor voxels A and B within this region are highlighted. Each voxel has a time activity curve signal $S_A$ and $S_B$ respectively (i.e. signal or image value as a function of time).

The optimization algorithm calculates, in a first step (e.g., based on a pre-defined model), the characteristic-times, which represent the two relevant peaks. For each characteristic-time the algorithm calculates a probability distribution P to accommodate with uncertainties. In this example, the characteristic-time maximal probabilities for the voxel A are around $t^0_{A1}$ and $t^0_{A2}$ for the first and second peaks respectively.

The algorithm calculates pre-defined arguments for each peak, i.e. $\text{arg}_1(t^0_{A1})$ and $\text{arg}_2(t^0_{A2})$ or more. For example, the required arguments may be the maximal gradients at the vicinity of $t^0_{A1}$ and $t^0_{A2}$. For each voxel, a relation function $F_v$ between the two (or more in principle) arguments is calculated. For example, the function may be defined by $\text{arg}_2/(\text{arg}_1 + \text{arg}_2)$. A cost function is calculated for the whole voxel-wise map. For example the cost function may be proportional to the variation magnitudes between neighbor voxels.

The optimization algorithm changes, during an optimization iterative process, the temporarily selected characteristic-times of the two peaks (for all voxels or part of them), and try to minimize the value of the map cost function and simultaneously to increase (maximize) the peak probability. The algorithm tries to find the best compromise between the two requirements (minimizing the map cost function and maximizing the characteristic-time probability).

In this example, the characteristic-times $t_{A1}$ and $t_{A2}$ are selected at an advanced iteration step instead of $t^0_{A1}$ and $t^0_{A2}$. In this case, the corresponding probabilities on $P_{A1}$ and $P_{A2}$ are lower but as a result the cost function on $F_v$ is also lower (i.e. better) if the difference between $F_{vA}$ to $F_{vB}$ is smaller than at the beginning. In the illustration, $t^0_{B1}$ and $t^0_{B2}$ were not changed, but of course in general they can be changed as well.

In a variation, the blood-flow peak can be defined by more than one variable than the characteristic-time. In yet another version, the peak arguments themselves can be associated with direct calculated probabilities which can be used for the optimization process without needing the characteristic-time definition.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A perfusion imaging data processor, comprising:
   a processor, including:
      an agent peak characteristic-time determiner configured to determine two or more agent peak characteristic-times respectively for two or more circulatory sub-systems represented in a same sub-set of voxels of a set of time-series data of perfusion imaging data;
      an agent peak argument determiner configured to determine an agent peak argument for each of the two or more agent peak characteristic-times;
      an agent peak argument relation determiner configured to determine a relationship between the agent peak arguments of the two or more agent peak characteristic-times; and
      a perfusion map generator configured to generate, based on the determined relationship and the perfusion imaging data, at least one perfusion map, wherein the at least one perfusion map includes volumetric image data visually presenting at least one of a relationship or a difference between the two or more circulatory sub-systems.

2. The processor of claim 1, wherein the processor further comprises:
   a probability distribution determiner configured to determine a probability distribution of each of two or more agent peak characteristic-times, wherein each probability distribution corresponds to one circulatory sub-system,
   wherein the probability distribution of one of the two or more agent peak characteristic-times represents a probability that a corresponding peak of the one of the two or more agent peak characteristic-times is a true peak of the circulatory sub-system, and
   wherein the peak argument determiner determines an agent peak argument for one of the circulatory sub-systems based on a selected one of the agent peak characteristic-times from a plurality of agent peak characteristic-times of the same circulatory sub-system.

3. The processor of claim 1, wherein the agent peak characteristic-time determiner determines the two or more agent peak characteristic-times based on a first model, which includes an algorithm for determining an agent peak characteristic-time.

4. The processor of claim 1, wherein the peak argument determiner determines the peak arguments based on a second model, which includes an algorithm for determining peak arguments.

5. The processor of claim 1, wherein the agent peak characteristic-time determiner iteratively determines the two or more agent peak characteristic-times, wherein, in one or more iterations, an agent peak characteristic-time is determined based on a previously determined agent peak characteristic-time.

6. The processor of claim 5, wherein the agent peak argument relation determiner iteratively determines the relationship between the agent peak arguments, wherein, in one or more iterations, an agent peak argument relation is determined based on an agent peak characteristic-time generated during the same iteration.

7. The processor of claim 5, wherein, in one or more iterations, a compliance of the peaks is checked against a model including peak constraints and consistency criteria.

8. The processor of claim 1, wherein the perfusion map generator iteratively determines the signal, wherein, in one or more iterations, the agent peak argument relation determiner determines a relationship between agent peak arguments for different agent peak characteristic-times, and the perfusion map generator iteratively determines the signal for each determined relationship.

9. The processor of claim 8, wherein, in one or more iterations, at least one different agent peak characteristic-time is utilized, and the at least one different agent peak characteristic-time corresponds to an agent peak characteristic-time that improves map image conditions subject to one or more of a pre-determined constraint or a cost function.

10. The processor of claim 8, wherein, in one or more iterations, at least one different agent peak characteristic-time is utilized, and the at least one different agent peak characteristic-time corresponds to an agent peak characteristic-time that increases a total probability of the agent peak characteristic-time.

11. The processor of claim 1, wherein the agent peak argument includes at least one of a peak intensity, a peak gradient, or information about a region around a peak.

12. The processor of claim 1, further comprising:
   an image processor configured to visually present the perfusion map, wherein the perfusion map visually presents at least one of separate images or superimposed images, wherein each of the images corresponds to at least one of a different circulatory sub-systems, a relationship between the circulatory sub-systems, or a difference between the circulatory sub-systems.

13. The processor of claim 12, wherein at least one of the relationship or the difference between the two or more circulatory sub-systems is visually emphasized using different colors.

14. The processor of claim 12, wherein other information corresponding to the two or more circulatory sub-systems is also visually presented in one or more of a graph, a histogram or a table.

15. A method, comprising:
   determining, with a processor, at least one of a relationship or a difference between agent peak arguments corresponding to two or more agent peak characteristic-times, which correspond to two or more different circulatory sub-systems represented in a same sub-set of voxels of a set of time-series data of perfusion imaging data, based on the same sub-set of voxels; and
   visually presenting at least one of the relationship or the difference.

16. The method of claim 15, further comprising:
   determining a probability distribution of each of two or more agent peak characteristic-times where each probability distribution corresponds to one circulatory sub-system, wherein the probability distribution of one of the two or more agent peak characteristic-times represents a probability that a corresponding peak of the one of the two or more agent peak characteristic-times is a true peak of the circulatory sub-system; and determining at least one of the agent peak arguments based on a selected one of the agent peak characteristic-times from a plurality of agent peak characteristic-times of the same circulatory sub-system.

17. The method of claim 15, further comprising:
iteratively determining the two or more agent peak characteristic-times, wherein, in one or more iterations, an agent peak characteristic-time is determined based on a previously determined agent peak characteristic-time.

18. The method of claim 15, further comprising:
determining at least one perfusion map based on the at least one of the relationship or the difference, wherein the at least one perfusion map includes volumetric image data that visually presents the at least one of relationship or difference between the two or more circulatory sub-systems.

19. The method of claim 18, further comprising:
iteratively determining the perfusion map, wherein, in one or more iterations, the perfusion map is generated based on a relationship or difference between agent peak arguments for different agent peak characteristic-times.

20. The method of claim 19, wherein, in one or more iterations, at least one different agent peak characteristic-time is utilized, and the at least one different agent peak characteristic-time corresponds to an agent peak characteristic-time that increases a total probability of the contrast material peak characteristic-time and/or improves map image conditions subject to one or more of a pre-determined constraint or a cost function.

21. The method of claim 15, wherein the agent peak arguments includes at least one of a peak intensity, a peak gradient, or information about a region around a peak.

22. The method of claim 15, wherein the at least one of the relationship or the difference is visually presented in separate images or superimposed to form a same image.

23. A non-transitory computer readable medium encoded with computer executable instructions which when executed by a processor cause the processor to:
determine at least one of a relationship or a difference between agent peak arguments corresponding to two or more agent peak characteristic-times, which correspond to tissue represented in a same sub-set of voxels of a set of time-series data of perfusion imaging data, based on the same sub-set of voxels;
generate a perfusion map including imaging data which visually illustrates at least one of the relationship or the difference; and
visually present perfusion map.

24. The non-transitory computer readable medium of claim 23, wherein the two or more agent peak characteristic-times correspond to agents in two or more different circulatory sub-system of a subject.

25. The non-transitory computer readable medium of claim 23, wherein the two or more agent peak characteristic-times correspond to a same circulatory sub-system of a subject.

* * * * *